United States Patent
Rasenick et al.

(10) Patent No.: US 7,445,888 B2
(45) Date of Patent: Nov. 4, 2008

(54) METHODS FOR ASSAYING FOR ANTIDEPRESSANT THERAPY MARKERS

(75) Inventors: Mark M. Rasenick, Glenview, IL (US); Robert J. Donati, Chicago, IL (US); Sadamu Toki, Hokkaido (JP)

(73) Assignee: The Board of Trustees of The University of Illinois, Urbana, IL (US)

( * ) Notice: Subject to any disclaimer, the term of this patent is extended or adjusted under 35 U.S.C. 154(b) by 23 days.

(21) Appl. No.: 11/529,944

(22) Filed: Sep. 29, 2006

(65) Prior Publication Data

US 2007/0026385 A1 Feb. 1, 2007

Related U.S. Application Data

(63) Continuation of application No. 11/053,516, filed on Feb. 8, 2005, now Pat. No. 7,118,858, which is a continuation of application No. 09/918,230, filed on Jul. 30, 2001, now Pat. No. 6,875,566.

(60) Provisional application No. 60/221,874, filed on Jul. 29, 2000.

(51) Int. Cl.
*C12Q 1/00* (2006.01)

(52) U.S. Cl. ............................ 435/4; 435/29

(58) Field of Classification Search .................. 435/4, 435/29
See application file for complete search history.

(56) References Cited

U.S. PATENT DOCUMENTS

| 6,034,071 | A | 3/2000 | Iyengar |
| 6,071,722 | A | 6/2000 | Elshourbagy et al. |
| 6,107,076 | A | 8/2000 | Tang et al. |
| 6,448,377 | B1 | 9/2002 | Kobilka et al. |
| 6,875,566 | B2 * | 4/2005 | Rasenick et al. ............ 435/4 |
| 7,118,858 | B2 * | 10/2006 | Rasenick et al. ............ 435/4 |
| 2002/0061599 | A1 | 5/2002 | Elling et al. |

FOREIGN PATENT DOCUMENTS

WO WO-97/20211 6/1997

OTHER PUBLICATIONS

Chen, J. Pharm. Exp. Ther., 275(1):509-517 (1995).
Chen, J. Neurochem., 64(2):724-732 (1995).
Young, J. Affect. Dis., 39(3):201-206 (1996).
Rasenick, J. Clin. Psychiatry, 57(Suppl 13):49-55 (1996).
Kamada, Cell. Mol. Neurobiol., 19(1):109-117 (1999).
Avissar et al., Pharmacopsychiat., 25:44-50 (1992).
Carlson et al., Mol. Pharmacol., 30:463-468 (1986).
Chen et al., J. Pharm. Exp. Ther., 275:509-517 (1995).
Chen et al., J. Neurochem., 64:724-732 (1995).
Cowburn et al., Brain Res., 633:297-304 (1994).
De Montis et al., Eur. J. Pharmcol., 180:169-174 (1990).
Donati et al., Mol. Pharm., 59:1426-1432 (2001).
Duman et al., Arch. Gen. Psychiatry, 54:597-606 (1997).
Emamghoreishi et al., Neuropsychopharmacology, 15:281-287 (1996).
Jenkinson et al., Br. J. Pharmacol., 126:131-136 (1999).
Kuo et al., Science, 260:232-234 (1993).
Lee et al., Methods Enzymol., 237:146-164 (1994).
Li et al., J. Biol. Chem., 270:15693-15701 (1995).
Menkes et al., Science, 219:65-67 (1983).
Neubig, J. FASEB, 8:939-946 (1994).
Okamoto et al., J. Biol. Chem., 273:5419-5422 (1998).
Ozawa et al., J. Neurochem., 56:330-338 (1991).
Ozawa et al., Mol. Pharm., 36:803-808 (1989).
Perez et al., Neuropsychopharmacology, 4:57-64 (1991).
Perez et al., Eur. J. Pharmacol., 172:305-316 (1989).
Popova et al., J. Neuroscience, 20:2774-2782 (2000).
Popova et al., J. Biol. Chem., 272:6760-6765 (1997).
Rasenick et al., J. Clin. Psychiatry, 57:49-55 (1996).
Rasenick et al., FEBS Lett., 207:296-301 (1986).
Rasenick et al., Brain Res., 488:105-113 (1989).
Rasenick et al., Adv. Second Messenger Phophoprotein Res., 24:381-386 (1990).
Rasenick et al., Nature, 294:560-562 (1981).
Regula et al., Ann. N.Y. Acad. Sci., 466:832-842 (1986).
Roychowdhury et al., J. Biol. Chem., 274:13485-13490 (1999).
Roychowdhury et al., Biochem., 32:4955-4961 (1993).
Roychowdhury et al., Biochem., 33:9800-9805 (1994).
Senda et al., "Alterations in the Detergent Extraction of G Protein from the Plasma Membrane From Postmortem Human Brains of Patients with Depression," Society for Neuroscience Abstracts, 26(1-2):Abstract (2000);30.sup.th Annual Meeting of the Society of Neuroscience, New Orleans, LA, USA, (Nov. 4-9, 2000).
Southwell et al., Cell Tissue Res., 292:37-45 (1998).
Sulser, Adv. Biochem. Psychopharmol., 39:249-261 (1984).
Takahashi et al., J. Neuroscience, 19:610-618 (1999).
Toki et al., J. Neurochem., 73:1114-1120 (1999).
Wang et al., Biochem., 30:10957-10965 (1991).
Yan et al., J. Neurochem., 66:1489-1495 (1996).
Yan et al., J. Neurochem., 76:182-190 (2001).

* cited by examiner

*Primary Examiner*—Ralph Gitomer
(74) *Attorney, Agent, or Firm*—Marshall, Gerstein & Borun LLP

(57) ABSTRACT

The present invention relates generally to methods for assaying for agents that modify the association of $G_{s\alpha}$ with components of the plasma membrane or cytoskeleton of cells. The present invention also relates generally to methods of assaying for agents having antidepressant activity via analysis of the association of $G_{s\alpha}$ with components of the plasma membrane or cytoskeleton of cells using a fluorescent analog of $G_{s\alpha}$ and fluorescence resonance energy transfer (FRET).

5 Claims, 9 Drawing Sheets

FIG. 3A
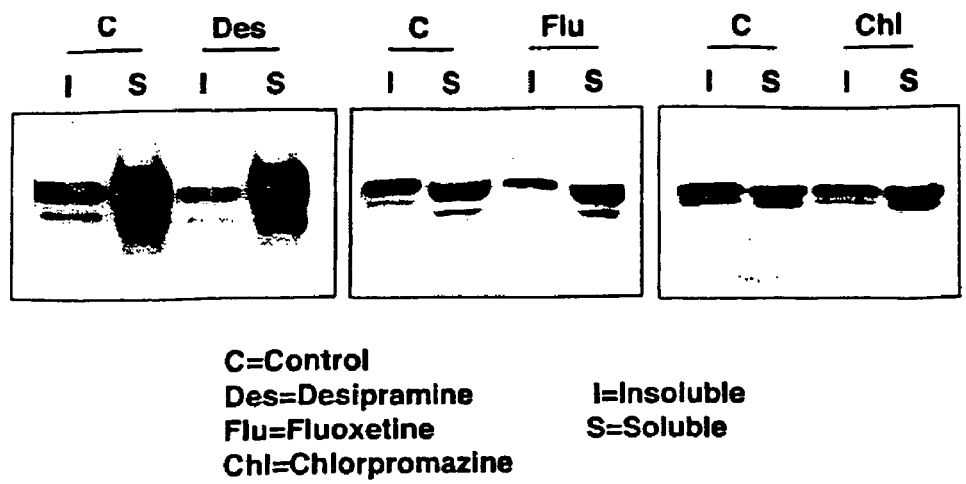
C=Control
Des=Desipramine
Flu=Fluoxetine
Chl=Chlorpromazine
I=Insoluble
S=Soluble
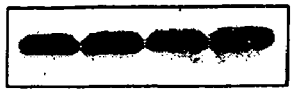
FIG. 3B
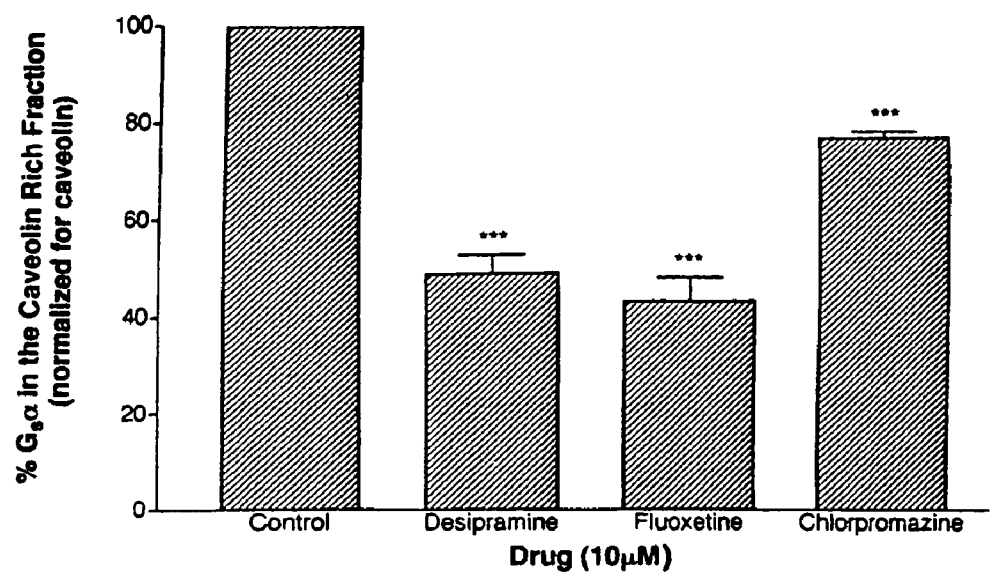
FIG. 3C

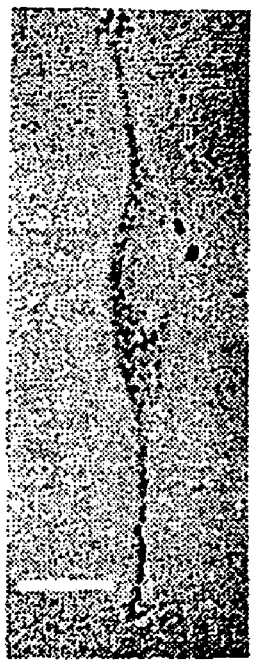
FIG. 5A
FIG. 5B

 
FIG. 9A  FIG. 9B
 
FIG. 9C  FIG. 9D

METHODS FOR ASSAYING FOR ANTIDEPRESSANT THERAPY MARKERS

The present application is a continuation of U.S. patent application Ser. No. 11/053,516, which was filed on Feb. 8, 2005 and is now U.S. Pat. No. 7,118,858, which is a continuation of U.S. patent application Ser. No. 09/918,230, which was filed Jul. 30, 2001 and is now U.S. Pat. No. 6,875,566, which claimed benefit of priority of U.S. Provisional Appl. No. 60/221,874, filed Jul. 29, 2000. Each of the aforementioned applications is specifically incorporated herein by reference in its entirety.

Certain of the studies described in the present application were conducted with the support of government funding in the form of a grant from the National Institutes of Health, Grant No. MH039595 and MH057391. The United States government may have certain rights in the invention.

BACKGROUND OF THE INVENTION

1. Field of the Invention

This invention relates generally to methods for determining the effectiveness of antidepressant therapy in a depressed individual as well as methods for detecting agents that possess antidepressant activity.

2. Related Technology

Affective disorders are characterized by changes in mood as the primary clinical manifestation. Major depression is one of the most common mental illnesses and is often under diagnosed and frequently undertreated, or treated inappropriately. Major depression is characterized by feelings of intense sadness and despair, mental slowing and loss of concentration, pessimistic worry, agitation, and self-deprecation. Physical changes usually occur that include insomnia, anorexia and weight loss (or overeating) decreased energy and libido, and disruption of the normal circadian rhythms of activity, body temperature, and many endocrine functions. As many as 10-15% of individuals with this disorder display suicidal behavior during their lifetime.

Antidepressant therapies are present in many diverse forms, including tricyclic compounds, monoamine oxidase inhibitors, selective serotonin reuptake inhibitors (SSRIs), atypical antidepressants, and electroconvulsive treatment. Antidepressant therapies vary widely in efficacy and the response of any given patient to a therapy is unpredictable. Unfortunately, therapy often proceeds for 1-2 months before it is established whether or not a specific modality of treatment is effective. Thus, there remains a need for methods of ascertaining where the antidepressant therapy is effective in a depressed individual as well as a need for a method of screening for novel antidepressant agents.

SUMMARY OF THE INVENTION

The present invention is directed to methods for determining the effectiveness of ongoing antidepressant therapy (during the early stages of therapy) by whether there has been a modification of the association of $G_{s\alpha}$ with components of the plasma membrane or cytoskeleton of cells from peripheral tissues of the depressed individual.

Another aspect of the invention is directed to methods involved in screening for effective antidepressant agents via their ability to alter (as compared to a control) the association of $G_{s\alpha}$ with components of the plasma membrane or cytoskeleton of cultured cells expressing Type VI adenylyl cyclase.

Other objectives and advantages of the invention may be apparent to those skilled in the art from a review of the following detailed description, including any drawings.

BRIEF DESCRIPTION OF THE DRAWINGS

FIG. 3 demonstrates that antidepressant treatment of C6-2B cells causes a shift in the localization of $G_{s\alpha}$ from a Triton X-100-insoluble caveolin-enriched domain to a more Triton X-100-soluble domain.

FIG. 5 demonstrates that chronic desipramine treatment of C6-2B glioma cells does not alter the overall shape of the cell. Cells were treated and processed for microscopy as described. A representative image of five independent experiments is shown. Bar, 10 µm.

FIG. 9 shows that $G_{o\alpha}$ does not undergo antidepressant induced relocalization. Untreated (A and B) and desipramine-treated© and D) cells show similar $G_{o\alpha}$ immunofluorescence profiles. There is staining throughout the cell body and processes of both sets of cells. The figure is typical of approximately 500 cells that were examined. Bar, 10 µm.

DETAILED DESCRIPTION OF THE INVENTION

Figure 1:
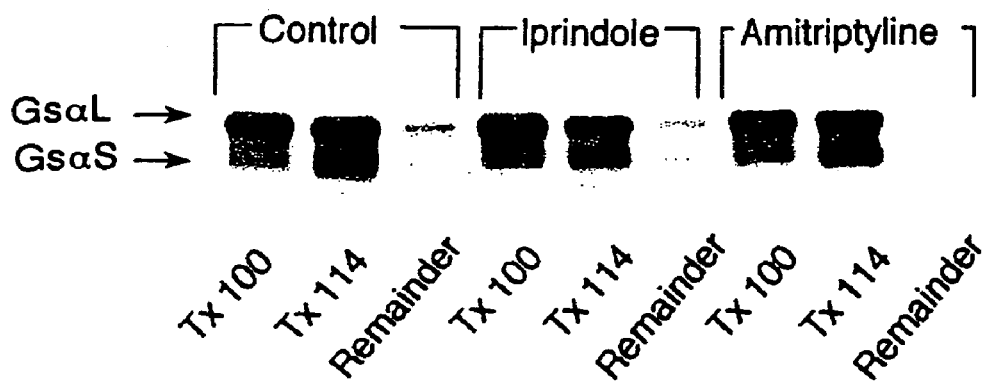
FIG. 1 shows detergent extraction of $G_{s\alpha}$ from C6-2B glioma membranes treated with antidepressants.

Despite several decades of studies, the mechanism of antidepressant action has not been clearly established. One of the most widely known biochemical effects of antidepressant treatment is an alteration in the density and/or sensitivity of several neurotransmitter receptor systems [Sulser, *Adv. Biochem. Psychopharmacol.*, 39:249-261; 1984]). However, these effects do not fully explain the clinical efficacy of all antidepressants, mainly because of the dissociation between the time course of the change in the receptor numbers and their clinical time course [Rasenick et al., *J. Clin. Psychiatry*, 57:49-55; 1996].

Many studies searching for a common mechanism of antidepressant action have focused on postreceptor neuronal cell signaling processes as potential targets of such action [Menkes et al. *Science*, 219:65-76, 1983; Ozawa et al., *Mol. Pharmacol.*, 36:803-808, 1989; Duman et al., *Arch. Gen. Psychiatry*, 54:597-606, 1997; Takahashi et al., *J. Neurosci.*, 19:610-616, 1999]. Much of this previous work has focused on the downstream effects of antidepressant action, particularly those involving cAMP [Perez et al., *Eur. J. Pharmacol.*, 172: 305-316, 1989; Perez et al., *Neuropsychopharmacology*, 4:57-64, 1991; Duman et al., *Arch. Gen. Psychiatry*, 54:597-606, 1997; Takahashi et al., *J. Neurosci.*, 19:610-616, 1999]. Our focus is on the upstream events occurring at the postsynaptic membrane involving G proteins and adenylyl cyclase.

Much of the current thinking about G protein-coupled receptors is based on the idea of freely mobile receptors, G proteins, and effectors in which the specificity of their interaction is derived from the three-dimensional structure of the sites of protein-protein interactions. However, recent evidence indicates that an organized interaction of receptors, G proteins, and effectors with significant limitations on lateral mobility [Kuo et al., *Science*, 260:232-234; 1993]. Furthermore, these membrane proteins are associated with tubulin or other cytoskeletal proteins [Carlson et al., *Mol. Pharmacol.*, 30:463-468, 1986; Rasenick et al., *Adv. Second Messenger Phosphoprotein Res.*, 22:381-386, 1990; Wang et al., *Biochemistry*, 30:10957-10965, 1991), which restrict distribution and mobility of G proteins to a surprising degree [Neubig, *FASEB*, 8:939-946; 1994]. These presence of a well organized network of cytoskeletal elements and the components of neurotransmitter and hormonal G protein-mediated signal transduction systems may play an important role in achieving this function.

Increasing evidence suggests that many species of heterotrimeric G proteins are present in caveolin-enriched membrane domains, and caveolin has been implicated as playing a major role in G protein-mediated transmembrane signaling [Okamoto et al., *J. Biol. Chem.*, 273:5419-5422, 1998]. Furthermore, Li et al. [J. Biol. Chem., 270:15693-15701, 1995] reported that the mutational or pharmacological activation of $G_{s\alpha}$ prevents its cofractionation with caveolin. Our data indicates that antidepressant treatment of C6-2B cells causes a shift in the localization of $G_{s\alpha}$ from a caveolin-enriched domain to a more Triton X-100-soluble fraction (e.g., see FIG. 3). Such data are consistent with the our finding that chronic antidepressant treatment alters the association between $G_{s\alpha}$ and some specific membrane component.

Multiple neural dysfunctions may exist in patients with depressive disorders, and there are likely to exist multiple molecular targets for antidepressants. The ability of different classes (data disclosed herein) of antidepressants to show the same effect on the redistribution of $G_{s\alpha}$ in the plasma membrane indicates convergence.

In view of the foregoing discussion and by way of illustration of the invention, the examples describe methods for determining the effectiveness of ongoing antidepressant therapy by whether there has been a modification of the association of $G_{s\alpha}$ with components of the plasma membrane or cytoskeleton of cells from peripheral tissues of the depressed individual as well as methods methods involved in screening for effective antidepressant agents via their ability to alter (as compared to a control) the association of $G_{s\alpha}$ with components of the plasma membrane or cytoskeleton of cultured cells expressing Type VI adenylyl cyclase.

The invention is illustrated by the following Examples, which are not intended to limit the scope of the invention as recited in the claims.

Example 1 provides methods and materials for experiments disclosed in Examples 2-8.

Example 2 describes results wherein the amount of $G_{s\alpha}$ in C6-2B glioma cell membranes is not altered by antidepressant treatment.

Example 3 provides results wherein detergent extraction of $G_{s\alpha}$ from C6-2B glioma membrane is increased by antidepressant treatment.

Example 4 sets forth results wherein detergent extraction of $G_{s\alpha}$ from C6-2B glioma membrane is increased by antidepressant treatment, with disparate antidepressants.

Example 5 provides results showing that antidepressant treatment increases Triton X-100 solubility of $G_{s\alpha}$ from rat synaptic membrane.

Example 6 provides results with respect to sucrose density sedimentation of adenylyl cyclase activity in control and desipramine-treated C6-2B cells Example 7 describes results showing that antidepressant treatment decreases the colocalization of $G_{s\alpha}$ with triton-insoluble, caveolin-enriched membrane domains and antidepressant-enhanced mobility is unique to $G_s$.

Example 8 sets forth results of experiments showing that antidepressant-enhanced mobility is unique to $G_{s\alpha}$.

Example 9 provides methods and materials for experiments disclosed in Examples 10-13.

Example 10 sets forth results from experiments showing that chronic antidepressant leads to a shift in cellular localization of $G_{s\alpha}$.

Example 11 provides results from experiments that show that antidepressant-induced G protein α subunit cellular relocalization is specific to $G_{s\alpha}$.

Example 12 sets forth results that show that (1) fluoxetine treatment also promotes $G_{s\alpha}$ migration and (2) chlorpromazine did not induce migration.

Example 13 sets forth methods for screening for the effectiveness of antidepressant therapy as well as screening for agents having antidepressant activity.

EXAMPLE 1

Methods and Materials

Set forth below are methods and materials for experiments disclosed in Examples 2-8.

Cell/Tissue Preparation

C6-2B cells (between passages 20 and 40) were grown in 175-cm$^2$ flasks in Dulbecco's modified Eagle medium, 4.5 g of glucose/L, 10% bovine serum, in a 10% $CO_2$ atmosphere, at 37° C. for 3 days after splitting. As 5 μM for 5 days and 10 μM for 3 days of antidepressant treatment had a similar effect on the Gpp(NH)p- or forskolin-stimulated adenylyl cyclase activity in the C6-2B cells [(Chen et al., *J. Neurochem.*, 64:724-732, 1995], the latter paradigm was used and cells were treated with 10 μM drug for 3 days. Media containing drugs (fluoxetine, amtriptyline, iprindole, desipramine, or chlorpromazine) were added to different flasks, and the media were changed daily. During the period of exposure to antidepressants, no morphological change in the cells was observed. After treatment, the cells were incubated in drug-free media for 1 h before harvesting by scraping with a rubber policeman in HEPES-sucrose buffer [15 mM HEPES, 0.25 M sucrose, 0.3 mM phenylmethylsulfonyl fluoride (PMSF), 1 mM EGTA, and 1 mM dithiothreitol (DTT), pH 7.5], C6-2B membranes were prepared as described [Rasenick and Kaplan, *FEBS Lett.* 207:296-301, 1986] and stored under liquid $N_2$ until use. Male Sprague-Dawley rats weighing 150-200 g were fed ad libitum and maintained in a 12-h light/dark cycle. The method of antidepressant treatment has been described previosuly [Ozawa and Rasenick, *Mol. Pharm.* 36:803-838, 1989]. In brief, animals were treated with desipramine or fluoxetine (10 mg/kg i.p.) once daily for 21 days; the control group received only saline injection daily for 21 days. Rat cerebral cortex membranes were prepared according to the method of Rasenick et al. [*Nature,* 294:560-562; 1981].

Membrane Protein Extraction

Membrane proteins were extracted sequentially from C6-2B or rat synaptic membranes as described [Yan et al., *J. Neurochem.,* 66:1489-1495; 1996]. These membranes were stirred on ice in HEPES (15 mM, pH 7.4) containing 1% Triton X-100 for 60 min followed by centrifugation at 100,000 g for 60 min at 4° C. The supernatant was reserved (Triton X-100 extract), and the resulting pellet was resuspended in Tris (15 mM, pH 7.4) containing 1.4% Triton X-114 and 150 mM NaCl. The solution was stirred for 60 min at 4° C. and centrifuged for 30 min at 100,000 g in the cold. The supernatant was saved (Triton X-114 extract). These supernatants and remaining pellet (remainder) were subjected to sodium dodecyl sulfate (SDS)-polyacrylamide gel electophoresis (PAGE) using 10% gels. All of the extraction buffers contained 1 mM PMSF and 1 mM EGTA.

Cell Fractionation by Sucrose Density Gradient Sedimentation

C6-2B cells treated as described above were used to prepare Triton-insoluble, caveolin-enriched membrane fractions by the procedure of Li et al. [*J. Biol. Chem.,* 270:15693-15701; 1995] with minor modifications. In brief, C6-2B cells were harvested into 0.75 ml of HEPES buffer (10 mM HEPES, pH 7.5, 150 mM NaCl, 1 mM DTT, 0.3 mM PMSF) containing 1% Triton X-100. Homogenization was carried out with 10 strokes of a Potter-Elvehjem homogenizer. The homogenate was adjusted to 40% sucrose by the addition of an equal volume of 80% sucrose prepared in HEPES buffer and placed at the bottom of an ultracentrifuge tube. A step gradient containing 30, 15, and 5% sucrose was formed above the homogenate and centrifuged at 50,000 rpm for 20 h in an SW65 rotor (240,000 g). Two or three opaque bands confined between the 15 and 30% sucrose layers were harvested, diluted threefold with HEPES buffer, and pelleted in a microcentrifuge at 16,000 g. The pellet was resuspended in HEPES buffer and identified as the Triton-insoluble fraction. The 40% sucrose region of the gradient was saved as the Triton-soluble fraction. In separate experiments, the same conditions were used, but instead of isolating the three opaque bands, 100-μl fractions were collected and assayed for $G_s$ content and adenylyl cyclase activity.

Assay of Adenylyl Cyclase Activity

Adenylyl cyclase was assayed as described previously [Rasenick et al., *Brain Res.,* 488:105-113; 1989]. Each sucrose gradient fraction was assayed under both basal and stimulated ($10^{-4}$ M forskolin) conditions for 10 min at 30° C. in 100 μl of medium containing 15 mM HEPES, pH 7.5, 0.05 mM ATP, [$\alpha$-$^{32}$P]ATP ($5 \times 10^6$ cpm/tube), 5 mM $MgCl_2$, 1 mM EGTA, 1 mM DTT, 0.5 mM cyclic AMP (cAMP), 60 mM NaCl, 0.25 mg/ml bovine serum albumin, 0.5 mM 3-isobutyl-1-methylxanthine, 1 U of adenosine deaminase/ml, and a nucleotide triphosphate regenerating system consisting of 0.5 mg of creatine phosphate, 0.14 mg of creatine phosphokinase, and 15 U of myosin kinase/ml. The reaction was stopped by addition of 0.1 ml of a solution containing 2% SDS, 1.4 mM cAMP, and 40 mM ATP, and the [$^{32}$P]cAMP formed was isolated by the method of Salomon (1979) using [$^3$H]cAMP to monitor recovery. All assays were performed in triplicate.

Immunoblotting

Rat cortex membrane, C6-2B cell membranes, or Triton extracts of each membrane preparation were subjected to SDS-PAGE followed by electrotransfer to polyvinylidene difluoride (PVDF) membrane. The PVDF membrane was incubated with a phosphate-buffered saline/Tween 20 Buffer (140 mM NaCl, 27 mM KCl, 81 mM $Na_2HPO_4$, 15 mM $KH_2PO_4$, 0.1% Tween 20, pH 7.4) and 3% bovine serum albumin. The membrane was then incubated with polyclonal rabbit antisera against the various G protein subunits [RM ($G_{s\alpha}$) or 116 ($G_{i1}$, $G_{i2}$, $G_{i3\alpha}$)] at a 1:25,000 (RM) or 1:5,000 (116) dilution (see below for source of antibodies). The PVDF membranes were washed three times and incubated with a dilution of 1:5,000 of the second antibody [horseradish peroxidase-linked anti-rabbit IgG F(ab')$_2$ (Amersham)]. Immunoreactivity was detected with an enhanced chemiluminescence (ECL) western blot detection system (Amersham) in accord with the manufacturer's instructions. The developed autoradiographs were analyzed by densitometry.

G Protein Purification and Quantification $G_{s\alpha}$ (His) His$_6$ was purified, from *Escherichia coli* expressing the recombinant gene for that protein, by a modification of the method of Gilman [Lee et al., *Methods Enzymol.,* 237: 146-164; 1994]. In brief, the bacteria were grown overnight in an enriched medium (2% tryptone, 1% yeast extract, 0.5% NaCl, 0.2% glycerol, and 50 mM $KH_2PO_4$, pH 7.2) containing 50 μg/ml ampicillin 8 L (8×1 L in 2-L Erlenmeyer flasks). Bacteria were collected by centrifugation, cells were lysed by sonication, the cleared cell lysate was loaded onto a Ni-NTA resin column (QiaGen), and the protein was eluted with a step gradient of 20 to 60 mM imidazole. $G_{s\alpha}$ protein was purified further by high-performance liquid chromatography with Resource Q chromatography (Pharmacia) and hydroxylapatite chromatography. Fractions containing $G_{s\alpha}$ protein were identified by labeling with [$\alpha$-$^{32}$P]P$^3$-(4-azidoanalido)-P$^1$-5'-GTP and immunoblotting. The $G_{s\alpha}$ was >98% pure as identified by silver stain of the gels.

Purified recombinant $G_{s\alpha L}$ (long form of $G_{s\alpha}$; 1-10 ng/lane) was subjected to SDS-PAGE and transferred to PVDF membranes. The blots were incubated with antibody against $G_{s\alpha}$ (RM) and processed by ECL. Films were analyzed on a Molecular Dynamics densitometer, and the volume of each band was quantified and used to make a standard curve.

Materials and Data Analysis

All detergents were obtained from Pierce, Anti-G protein antibodies were from Drs. David Manning (116; University of Pennsylvania) and Allen M. Spiegel (RM; National Institutes of Health). Caveolin antibody was obtained from Transduction Laboratories (Lexington, Ky., U.S.A.) clone no 2297. All other reagents used were of analytical grade.

Further, antibodies for use in the protocols disclosed herein may also be manufactured by well known methods [*Antibodies, A Laboratory Manual*, Harlow and Lane, Cold Spring Harbor Laboratory; ISBN: 0879693142].

Data were analyzed for statistical significance using Scheffé's test or Bonferroni's multiple comparison test after a one-way ANOVA test or two-tailed t test. Values of $p<0.05$ were taken to indicate significance.

EXAMPLE 2

The Amount of $G_{s\alpha}$ in C6-2B Glioma Membrane is not Altered by Antidepressant Treatment Experiments were conducted to determine whether $G_{s\alpha}$ is quantitatively altered by antidepressant therapy. For quantification of $G_{s\alpha}$ in C6-2B membrane, a standard curve was created using purified recombinant $G_{s\alpha}$. Pure $G_{s\alpha}$ (1-20 ng/well) was subjected to SDS-PAGE and transferred to a PVDF membrane, $G_{s\alpha}$ was immunodetected by antisera against the αs subunit of G protein.

To estimate the effect of antidepressant treatment on the amount of $G_{s\alpha}$ in C6-2B membranes, equal amounts (10 μg) of C6-2B glioma membrane proteins in control and chronically (3 days) antidepressant-treated groups were subjected to SDS-PAGE. $G_{s\alpha}$ was immunodetected by antisera against the αs subunit of G protein. Table 1 summarizes the quantity of G proteins in the membrane of C6-2B cells after exposure to 10 μM (3 days) amitriptyline, iprindole, or fluoxetine (values are expressed as means±standard error of the mean of 4-5 experiments. As shown in Table 1, no significant differences were detected ($p>0.05$) between antidepressant-treated and control groups.

by immunodetection. A representative immunoblot (FIG. 1) shows the redistribution of $G_{s\alpha L}$ and $G_{s\alpha S}$ in the plasma membrane after chronic antidepressant treatment (i.e., the effect of the tricyclic antidepressant (amitriptyline) and an atypical, non-reuptake-inhibiting antidepressant (iprindole) on the redistribution). The data indicate $G_{s\alpha}$ was shifted to the less hydrophobic fraction (Triton X-100 extract) from the more hydrophobic fraction (Triton X-114 extract) subsequent to treatment with antidepressant $G_{s\alpha}$ exists in four splice variations that migrate as a long form ($G_{s\alpha L}$) and short form ($G_{s\alpha S}$) (the two long and two short variants are not resolved from one another). $G_{s\alpha L}$ in the Triton X-114 fraction was significantly lower in the iprindole- and amitriptyline-treated groups than in the control group. $G_{s\alpha S}$ also showed a tendency to migrate to the less hydrophobic domain (Triton X-100 extract) from a more hydrophobic domain of the plasma membrane.

EXAMPLE 4

Disparate Antidepressants Have Similar Effects

Experiments were conducted according to the method set forth in Example 1 to assess the effects of different antidepressants on the detergent extraction of $G_{s\alpha}$ from C6-2B glioma cells. Three different antidepressants comprised of the tricyclic antidepressant (amitriptyline), the non-reuptake inhibitor (iprindole), and SSRI (fluoxetine) were used. Membranes were prepared from C6-2B glioma cells that had been exposed to a 10 μM concentration of the indicated antidepressant drug for 3 days.

The ratios of the percentage of $G_{s\alpha}$ extracted by the two detergents in the treatment versus control groups were com-

TABLE 1

Effect of antidepressant treatment on the content of G protein in C6-2B glioma membranes

| Subunit of G protein | G protein amount (ng/10 μg of membrane protein) | | | |
| --- | --- | --- | --- | --- |
| | Control | Iprindole | Amitriptyline | Fluoxetine |
| αsL | 8.35 ± 0.05 | 8.20 ± 0.20 | 8.13 ± 0.17 | 7.23 ± 0.56 |
| αsS | 5.15 ± 0.28 | 4.70 ± 0.12 | 4.98 ± 0.21 | 5.65 ± 0.74 |
| Total | 13.50 ± 0.27 | 12.93 ± 0.36 | 13.10 ± 0.34 | 12.49 ± 0.67 |

EXAMPLE 3

Detergent Extraction of $G_{s\alpha}$ from C6-2B Glioma Membrane is Increased by Antidepressant Treatment In order to determine whether detergent extraction of $G_{s\alpha}$ from cells treated with antidepressants increased the following experiment was undertaken.

C6-2B cells were treated chronically with iprindole, amitriptyline, or chlorpromazine (10 μM, 3 days) and harvested. A membrane-enriched fraction was prepared (see Example 1), and membrane proteins were extracted sequentially with Triton X-100 (Tx 100) and Triton X-114 (Tx 114). Equal amounts of these extracts were subjected to SDS-PAGE and transferred to PVDF membrane. The long and short forms of $G_{s\alpha}$ ($G_{s\alpha L}$ and $G_{s\alpha S}$) from different fractions were identified pared and are set forth in Table 2 as percentage of control (i.e., each Triton X-100 extract was compared with the untreated Triton X-100 extract; the same was done for Triton X-114 extracts as well as the remainder). The values shown are means±standard error of the mean of 4-5 experiments.

The different antidepressants achieved similar effects on $G_{s\alpha}$, i.e., $G_{s\alpha}$ shifted to the less hydrophobic, Triton X-100 fraction subsequent to antidepressant treatment. In contrast, chlorpromazine, which is a tricyclic compound but not an antidepressant, did not exert these effects. The total amount of $G_{s\alpha}$ was not changed by antidepressant treatment, membrane preparation, or detergent extraction.

Other experiments showed that amphetamine, which is known to block neurotransmitter uptake but does not have antidepressant activity, was also without effect.

TABLE 2

Effects of antidepressants on detergent extraction of $G_{s\alpha}$ from C6-2B cells

| Antidepressant | $G_{s\alpha}$ subunit | % of corresponding value in control group | | |
|---|---|---|---|---|
| | | Extraction | | |
| | | Triton X-100 | Triton X-114 | Remainder |
| Iprindole | $G_{s\alpha L}$ | 128.0 ± 3.8[a] | 75.3 ± 2.2[b] | 87.7 ± 9.3 |
| | $G_{s\alpha S}$ | 146.6 ± 13.3[b] | 74.7 ± 0.9[b] | 112.0 ± 1.9[a] |
| Amitriptyline | $G_{s\alpha L}$ | 120.3 ± 3.7[b] | 84.5 ± 0.8[b] | 83.4 ± 14.5 |
| | $G_{s\alpha S}$ | 140.3 ± 9.3[b] | 92.7 ± 3.8 | 82.6 ± 5.1[a] |
| Fluoxetine | $G_{s\alpha L}$ | 146.4 ± 12.7[a] | 84.4 ± 2.9[b] | 90.8 ± 34.2 |
| | $G_{s\alpha S}$ | 215.9 ± 30.9[a] | 92.2 ± 1.3[b] | 99.7 ± 3.1 |
| Chlorpromazine | $G_{s\alpha L}$ | 107.4 ± 8.3 | 105.7 ± 6.5 | 83.8 ± 22.0 |
| | $G_{s\alpha S}$ | 113.4 ± 10.7 | 102.2 ± 15.6 | 100.4 ± 31.6 |

[a] $p < 0.05$,
[b] $p < 0.01$ by two-tailed t test

EXAMPLE 5

Antidepressant Treatment Increases Triton X-100 Solubility of $G_{s\alpha}$ from Rat Synaptic Membrane

Rats were treated with antidepressant via intraperitoneal injection once daily for 21 days, control animals received an equal number and volume of injection of saline. Cerebral cortices from each group were removed. Rat synaptic membrane-enriched fractions were prepared (see Example 1). The ratios of the percentage of $G_{s\alpha}$ extracted by the two detergents in the treatment versus control groups were compared and are set forth in Table 3 as percentage of control (i.e., each Triton X-100 extract was compared with the untreated Triton X-100 extract, the same was comparison was undertaken for Triton X-114 extracts as well as the remainder). The values shown are means±standard error of the mean of 4-6 experiments.

Results indicate that both desipramine and fluoxetine treatment caused a significant increase of $G_{s\alpha L}$ in the Triton X-100 extract and a concomitant decrease in that protein in the Triton X-114 extract. Under no circumstances did the antidepressant treatment alter the amount of $G_{s\alpha}$. The sum of $G_{s\alpha}$ immunoreactivity of the three fractions was not changed. Previous studies had demonstrated that a 1-day treatment of cells or a 1-week treatment of rats was without effect in any of the parameters examined [Ozawa et al., *J. Neurochem.*, 56:330-338, 1991; Chen et al., *J. Neurochem.*, 64:724-732, 1995]). Similar short-term treatments with fluoxetine were also without effect.

TABLE 3

Effects of chronic antidepressants on detergent extraction of $G_{s\alpha}$ from rat synaptic membrane

| Antidepressant treatment | $G_{s\alpha}$ Subunit | % of corresponding value in control group | | |
|---|---|---|---|---|
| | | Extraction | | |
| | | Triton X-100 | Triton X-114 | Remainder |
| Desipramine | $G_{s\alpha L}$ | 128.2 ± 9.5[a] | 77.3 ± 8.8[a] | 66.0 ± 10.2[a] |
| | $G_{s\alpha S}$ | 146.4 ± 9.6[b] | 71.7 ± 6.8[a] | 84.9 ± 25.7 |
| Fluoxetine | $G_{s\alpha L}$ | 118.1 ± 3.4[a] | 81.9 ± 4.5[a] | 53.8 ± 6.9[a] |
| | $G_{s\alpha S}$ | 153.8 ± 39.9 | 91.6 ± 6.3 | 45.2 ± 8.4[a] |

[a] $p < 0.05$,
[b] $p < 0.01$ by two-tailed t test.

EXAMPLE 6

Sucrose Density Sedimentation of Adenylyl Cyclase Activity in Control and Desipramine-Treated C6-2B Cells

Membranes from control and 10 μM desipramine-treated C6-2B glioma cells were solubilized in Triton X-100 and run on a discontinuous sucrose density gradient. Fractions were collected and assayed for adenylyl cyclase activity and for the presence of $G_{s\alpha}$ by SDS-PAGE and immunoblotting.

Figure 2A:
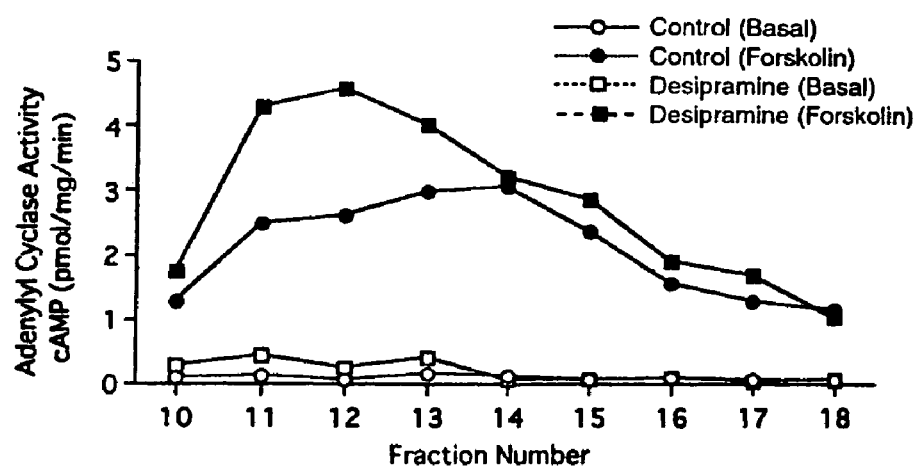
FIG. 2 shows co-localization of adenylyl cyclase activity with the presence of $G_{s\alpha}$ in Triton X-100-extracted C6-2B cells fractionated on a sucrose density gradient.
Figure 2B:
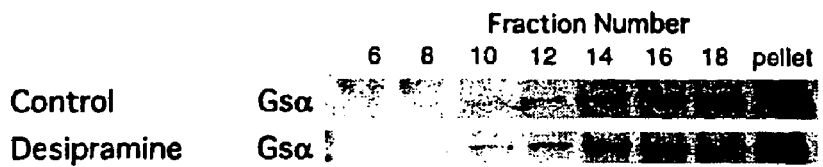

FIG. 2A shows adenylyl cyclase activity was measured on sucrose density gradient fractions from control (circles) and desipramine-treated (squares) C6-2B cells under basal (open symbols) and forskolin-stimulated (filled symbols) conditions. FIG. 2B shows a $G_{s\alpha}$ immunoblot corresponding to the assayed fractions in FIG. 2A.

FIG. 2A demonstrates an increase in forskolin-stimulated adenylyl cyclase activity for both control and desipramine-treated cells (note the corresponding increase in $G_{s\alpha}$ and adenylyl cyclase activity in fractions 10 and 12 of the desipramine-treated group). Further, there is almost a twofold increase in enzyme activity in the desipramine-treated cells compared with control in fractions 11 and 12. Basal adenylyl cyclase activity is unchanged in either group. The increase in forskolin-stimulated adenylyl cyclase activity corresponds to an increase in $G_{s\alpha}$ in these same fractions (FIG. 2B, fraction 12).

EXAMPLE 7

Antidepressant Treatment Decreases the Colocalization of $G_{s\alpha}$ with Triton-Insoluble, Caveolin-Enriched Membrane Domains and Antidepressant-Enhanced Mobility is Unique to $G_s$

Recently, it has been reported that caveolin, a Triton-insoluble membrane protein, participates in plasma membrane coupling events (Okamoto et al., *J. Biol. Chem.*, 273:5419-5422; 1998). To evaluate the interaction between $G_{s\alpha}$ and caveolin-enriched membrane domains, C6-2B cell lysates were subjected to sucrose density gradient fractionation and divided into a low-density, Triton X-100-insoluble fraction, which is dramatically enriched in caveolin, and a Triton X-100-soluble fraction, which contains the majority of other membrane proteins. Results are set forth in FIG. 3.

FIG. 3A reveals a set of representative immunoblots of the distribution of $G_{s\alpha}$ after sucrose density gradient fractionation. As shown, chronic antidepressant treatment of C6-2B cells causes a shift in the localization of $G_{s\alpha}$ from a caveolin-enriched domain to a more Triton X-100-soluble domain. The amount of $G_{s\alpha}$ in the soluble fraction of desipramine- and fluoxetine-treated cells was consistently three to five times greater than the amount in the caveolin-enriched fraction, making a direct measurement of the shift from one domain to the other nearly impossible. FIG. 3C shows the percent change in $G_{s\alpha}$ in the caveolin-enriched Triton-insoluble fraction normalized to equal caveolin. FIG. 3B shows a typical caveolin immunoblot used for this normalization. There was only a 5-10% difference in the amount of caveolin isolated in the Triton-insoluble domain between the experimental groups, and very little caveolin was found in the soluble fraction. Both desipramine and fluoxetine treatment decreased the amount of $G_{s\alpha}$ in the caveolin-enriched fraction by ~50%. In contrast, chlorpromazine caused a reduction of no more than 25% of $G_{s\alpha}$ in the caveolin-enriched fraction. Results were determined to be significant by one-way ANOVA (*p<0.0001), as well as Bonferroni's (*p<0.001) multiple comparison tests.

EXAMPLE 8

Antidepressant-Enhanced Mobility is Unique of $G_{s\alpha}$

Experiments were conducted (as described in Example 1) to ascertain the effect of antidepressant therapy on the mobility of $G_{i\alpha}$ from C6-2B glioma cells. Specifically, C6-2B cells were treated with fluoxetine (10 μM, 3 days) and harvested. A membrane-enriched fraction was prepared, and membrane protein was extracted sequentially with Triton X-100 (Tx 100) and Triton X-114 (Tx 114). Equal amounts of these extracts were subjected to SDS-PAGE and transferred to PVDF membrane. The PVDF membrane was incubated with polyclonal rabbit antisera against $G_{i\alpha 1}$, and $G_{i\alpha 2a}$. Immunoreactivity was detected with an ECL western blot detection system.

Figure 4:
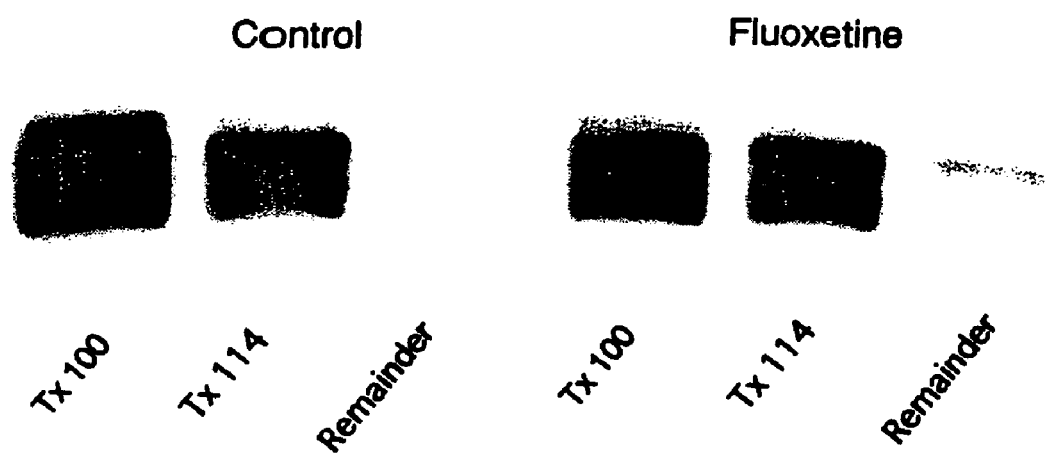
FIG. 4 shows fractional distribution of $G_{i\alpha}$ from C6-2B glioma membranes treated with fluoxetine.

Results, which are set forth in FIG. 4, indicated that unlike $G_{s\alpha}$, $G_{i\alpha}$ did not migrate to a less hydrophobic membrane fraction after antidepressant treatment.

EXAMPLE 10

Methods and Materials

Set forth below are method and materials used in experiments discussed in Examples 10-13.

Cell Culture

C6-2B cells (between passages 30 and 50) were plated onto coverslips and allowed to attach overnight in Dulbecco's modified Eagle's medium, 4.5 g/l glucose, 10% bovine serum, and 100 μg/ml penicillin and streptomycin at 37° C. in a humidified 10% $CO_2$ atmosphere. As reported previously, desipramine treatment regimens of 3 μM for 5 days and 10 μM for 3 days yielded similar biochemical results (Chen and Rasenick, 1995b). Therefore, the latter treatment paradigm was used in these experiments because it was easier to maintain the cell cultures for 3 days. In some instances, 10 μM fluoxetine was used. The culture media and drug were changed daily. Neither desipramine nor fluoxetine treatment altered cell growth (as determined by the confluence of the cell monolayer and total protein estimation) or cell viability (as determined by 4,6-diamidino-2-phenylindole staining and visualization under a fluorescence microscope with UV light). During the treatment duration, no morphological changes were observed in the cells. After the treatment duration, the cells were incubated in drug-free media for 45 to 60 minutes before fixation.

Indirect Immunofluorescence Laser Scanning Confocal Micros Copy

After treatment, cells were washed once with phosphate-buffered saline (PBS, 136 nM NaCl, 2.6 mM KCl, 5.4 mM $Na_3PO_4$ $7H_2O$, pH 7.4) and fixed with ice-cold methanol for 10 minutes. Cells were then washed three times with PBS followed by 2 h of blocking in 5% normal goat serum/0.2% fish skin gelatin in PBS. Primary antibody was added for 1.5 h, $G_{s\alpha}$/RM1 (PerkinElmer Life Sciences, Boston, Mass.) 1:50 and Goα (Santa Cruz Biotechnology, Santa Cruz, Calif.) 2 μg/ml, followed by three washes with PBS. Oregon Green-labeled secondary antibody (Molecular Probes, Eugene, Oreg.) was added at a concentration of 8 μg/ml for 1 h followed by three PBS washes. The coverslips were mounted onto slides with Vectashield (Vector Laboratories, Burlingame, Calif.) containing diamidino-2-phenylindole as a mounting medium. Images were acquired using a Zeiss LSM510 laser-scanning confocal microscope (Carl Zeiss Inc., Thornwood, N.Y.). A single 488-nm beam from an argon/krypton laser was used for excitation of the Oregon Green. Differential interference contrast images were also acquired. Five experiments were performed and coverslips were examined. Approximately 2100 cells from control and desipramine-treated coverslips were counted by two investigators blind to the experimental conditions over the course of the five experiments.

Fluorescence Quantification

The cellular distribution of $G_{s\alpha}$ was quantified in confocal imaged C6-2B cells using NIH-Image software (http://rsbin-fonihpov/nih-image) as describe previously [Southwell et al., Cell Tissue Res., 292:37-45, 1998; Jenkinson et al., Br. J. Pharmacol., 126:131-136, 1999]. Images of 9×1 μm optical, planar sections taken from four randomly selected control and four randomly selected desipramine-treated cells were captured and the middle five sections from each cell were quantified. Total cellular $G_{s\alpha}$ fluorescence was measured by counting the number of pixels with intensity above threshold (determined by minimum intensity above background in this case 50 pixels). The areas of intensity were numbered and divided visually into those localized to the cell body and those localized to the processes and process tips. The total from each region was divided by the total cell pixel intensity and expressed as a percentage of the total. This was done for each section of each cell and the sections were averaged per cell to give an average percentage total per cell.

In a separate investigation, seven sets of 300 cells each from control group and desipramine-treated cells from five experiments were counted to determine the primary localization (processes and process tips or cell body) of $G_{s\alpha}$ within these cells. The majority of the cells stained positively for $G_{s\alpha}$ throughout the entire cell, but there was usually an enhancement in one of these regions. Overly flattened and fragmented cells were omitted from counting, as were cells that did not display processes. The counts are expressed as the ratio of process and process tip localization/cell body localization.

Data Analysis

Images were evaluated by two investigators blinded to the treatment condition. Student's t test was performed for statistical analysis. Values of p<0.05 were taken to indicate significance.

EXAMPLE 10

Chronic Antidepressant Treatment Leads to a Shift in the Cellular Localization of $G_{s\alpha}$ Studies were conducted to determine whether a shift in cellular localization of $G_{s\alpha}$ occurred in C6-2B cells subjected to antidepressants. C6-2B glioma cells were treated with the tricyclic antidepressant desipramine (10 μM) for three days and were then examined by laser scanning confocal microscopy to visualize these changes in membrane localization (See Example 9 for specific experimental protocol).

Examination of 300 to 500 control and desipramine-treated cells by three independent researchers revealed that desipramine treatment did not alter the overall structure of C6-2B cells (FIG. 5), but drastically reduced the presence of $G_{s\alpha}$ in the process tips (FIG. 6, arrowheads and FIG. 7). In addition, there was an increase in the presence of $G_{s\alpha}$ within the cell body of many of the desipramine-treated cells (FIG. 6, arrows), as well as a decrease within the cell processes themselves (FIG. 6, asterisks). In some instances, there was an intense clustering of $G_{s\alpha}$ staining in the cell body (FIG. 6C, arrows), but the majority of the cells did not exhibit such a focal increase in $G_{s\alpha}$ staining.

Figure 8:
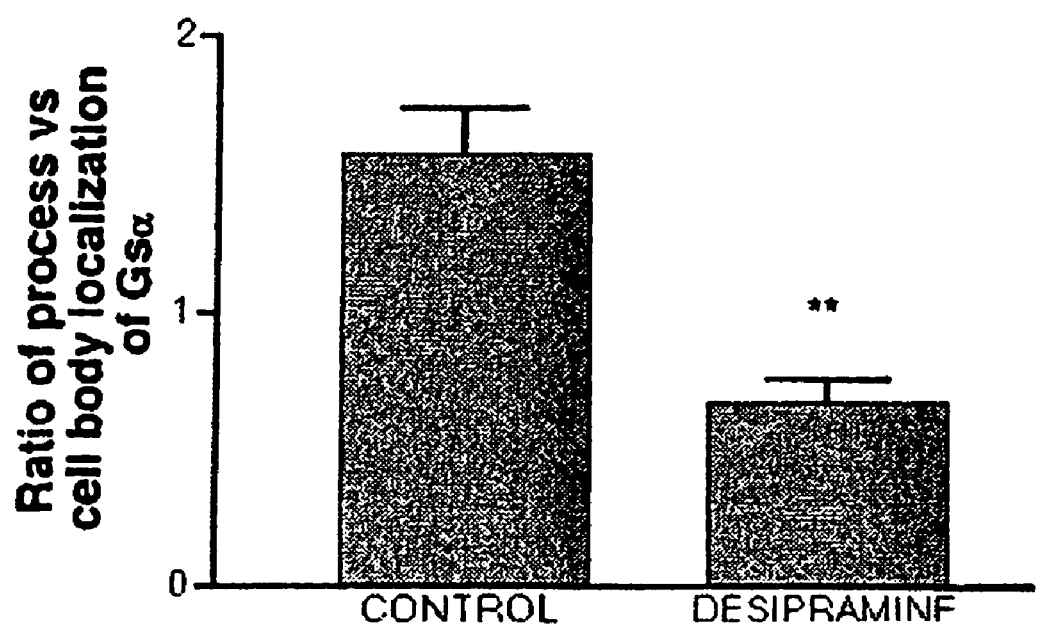
FIG. 8 demonstrates the qualitative differences between control and desipramine-treated cells demonstrate a loss of $G_{s\alpha}$ staining in the cell processes and process tips.

Twenty-one hundred cells from each group (control versus desipramine-treated) over a series of five experiments were examined to quantify the extent of the antidepressant effect. The cells were grouped into two categories: those that displayed intense staining at the process tips as well as overall staining in the processes and cell body (category A) versus those that displayed intense staining in the cell body region and decreased process and process tip staining (category B). Abnormal cells or those not displaying processes were not included in the cell count. Cells (300-450) were counted per experiment and the ratio of category A cells to category B cells for each group is shown in FIG. 8.

Twice as many control cells (64%) displayed $G_{s\alpha}$ staining at the process tips and throughout the entire cell than those treated with desipramine (32%). This demonstrates that $G_{s\alpha}$ relocalization is not an all-or-none response to antidepressant treatment and that some cells may be more responsive to treatment than others.

To determine quantitative differences between the groups, five 1 µm optical, planar sections through each of four cells in each group were examined by confocal microscopy and the digital images were captured. These images were then analyzed using the program NIH Image [Southwell et al., *Cell Tissue Res.*, 292:37-45, 1998; Jenkinson et al., *Br. J. Pharmacol.*, 126:131-136, 1999]. These experiments were undertaken to account for changes in $G_{s\alpha}$ localization at different focal planes of the cell. The percentage of $G_{s\alpha}$ localized to the cellular processes and process tips of control versus treated cells were compared by dividing the pixel density above threshold in these regions by the total cellular pixel density (Table 4). There was a three-fold decrease in $G_{s\alpha}$ localization to the processes and process tips between control cells and desipramine-treated cells as 12% of the total cellular $G_{s\alpha}$ was located in the process tips of control cells versus 4% present in the tips after desipramine treatment.

TABLE 4

Percentage of $G_{s\alpha}$ Immunofluorescence Distribution in the Cell

| Sample Control | Cell Body | Processes |
|---|---|---|
| C1 | 83.9 | 16.1 |
| C2 | 89.0 | 11.0 |
| C3 | 83.5 | 16.5 |
| C4 | 95.6 | 4.4 |
| Average | 88.0 ± 5.7 | 12.0 ± 5.7 |
| Desipramine | | |
| D1 | 91.4 | 8.6 |
| D2 | 92.2 | 7.8 |
| D3 | 100.0 | 0.0 |
| D4 | 100.0 | 0.0 |
| Average | 95.9 ± 4.7 | 4.1 ± 4.7 |

EXAMPLE 11

Antidepressant Induced G Protein α Subunit Cellular Relocalization is Specific to $G_{s\alpha}$ To determine whether antidepressant-induced mobility is specific to $G_{s\alpha}$, $G_{o\alpha}$ distribution was examined in approximately 500 cells under the same treatment conditions. FIG. 9 shows that there was little if any change in the distribution of $G_{o\alpha}$ after desipramine treatment. $G_{o\alpha}$ is throughout the cell without specific regions displaying an increased staining intensity in control or treated cells. Some of the control cells (FIGS. 9A and 9B) have a slight increase in staining intensity at the process tips, but this is also seen in the treated cells (FIGS. 9C and 9D), indicating that antidepressant treatment does not effect $G_{o\alpha}$ localization within the cell.

EXAMPLE 12

Fluoxetine Treatment also Promotes $G_{s\alpha}$ Migration

Figure 6A:
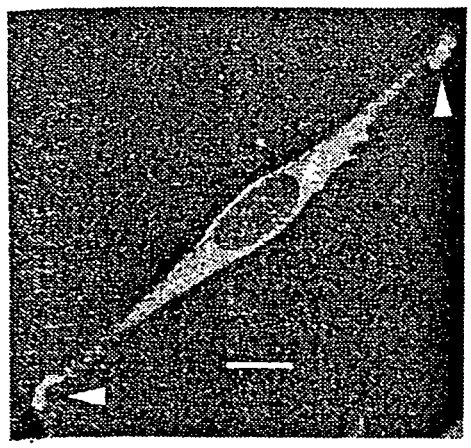
FIG. 6 shows that chronic desipramine treatment results in an enhancement of $G_{s\alpha}$ immunofluorescence in the cell body and a decrease in the cell processes and process tips. Untreated CD-2B glioma cells (A and B) display ubiquitous staining of $G_{s\alpha}$ with an enhancement at the process tips (arrowheads) and cell processes (asterisks). Desipramine treated cells C and D) show a decrease in $G_{s\alpha}$ staining at the process tips (arrowheads) and cell processes (asterisks) and simultaneously display an increase in cell body staining (arrows). Cells were treated and prepared for microscopy as described previously. Bar=10 µm.
Figure 6B:
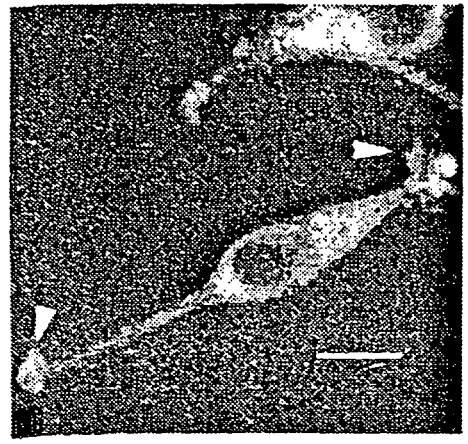
Figure 6C:
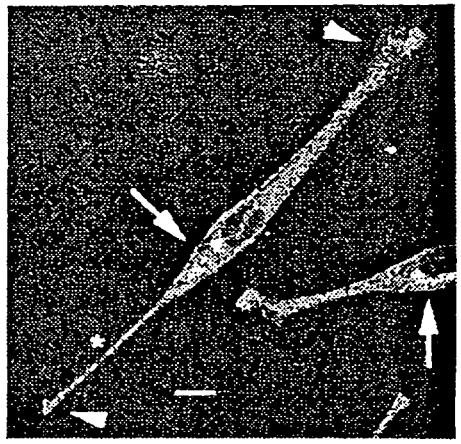
Figure 6D:
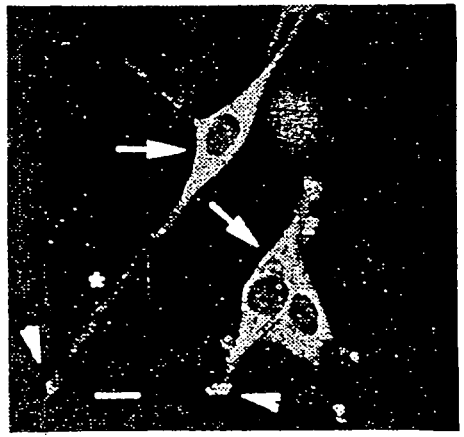
Figure 7A:
FIG. 7 shows an enlarged view of the process tips in control versus desipramine treated C6-2B cells shown in FIG. 6. The process tips from the control cell in FIG. 6A were enlarged to show the intense $G_{s\alpha}$ staining (A and B) and the corresponding process tips of the desipramine treated cell in FIG. 6C are shown to demonstrate the reduction of $G_{s\alpha}$ staining after antidepressant treatment© and D).
Figure 7C:
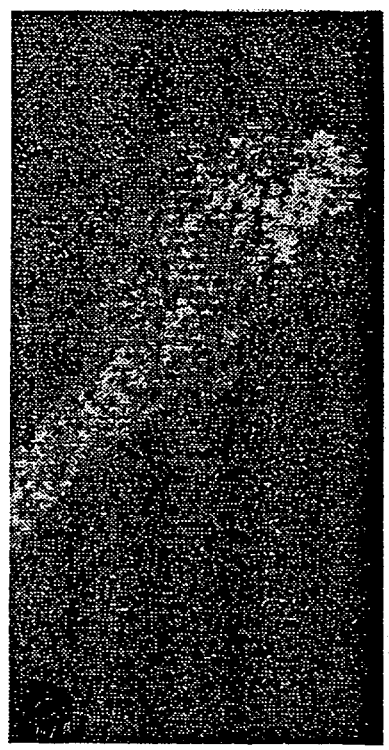
Figure 7B:
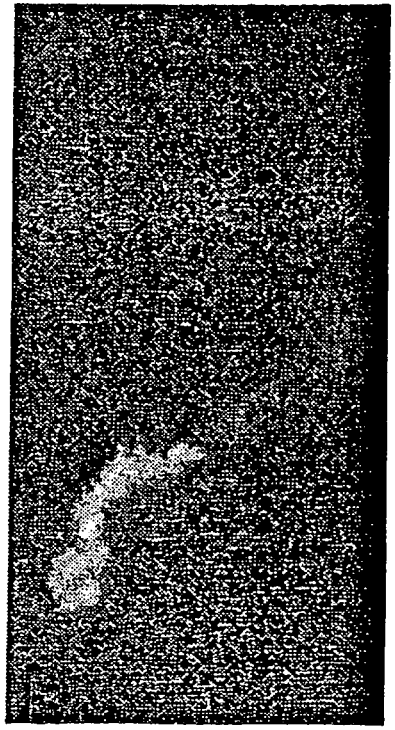
Figure 7D:
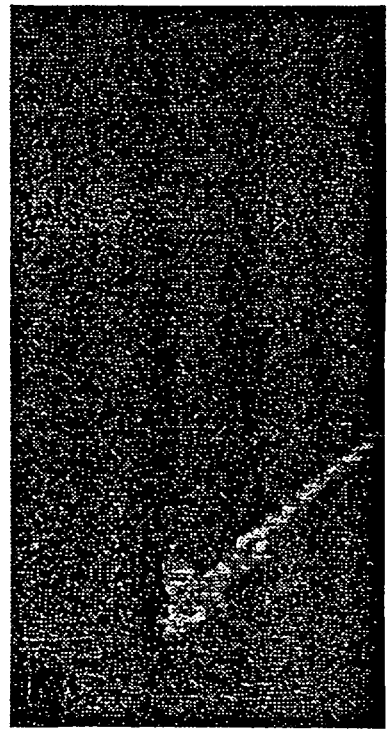
Figure 10A:
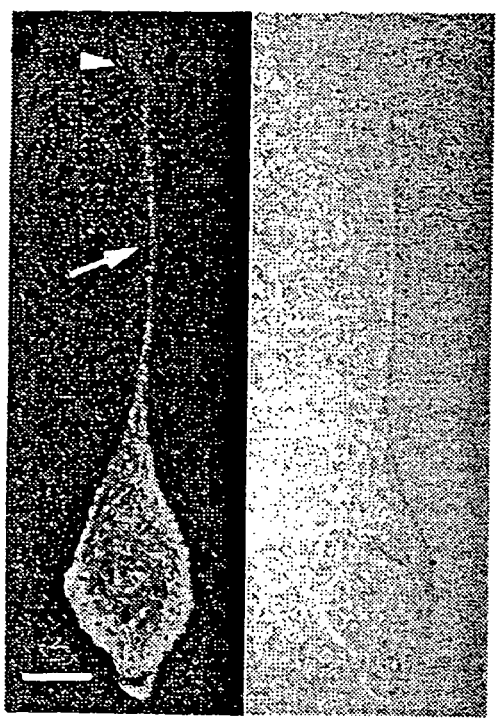
FIG. 10 shows that fluoxetine (10 µM) treatment for 3 days has effects similar to those of desipramine on $G_{s\alpha}$ cellular localization. Cells were treated with fluoxetine (A) or chlorpromazine (B) and processed for confocal microscopy as described. Like desipramine, fluoxetine treatment results in a drastic reduction of $G_{s\alpha}$ immunofluorescence in the cell process (arrow) and process tips (arrowhead), whereas chlorpromazine treatment results in a uniform distribution of Gsα similar to control (compare to FIG. 6, A and B). The differential interference contrast image to the right of the fluorescence image shows that these drugs have no effect on global cell shape. Bar, 10 µm.

If the redistribution of $G_{s\alpha}$ is truly an antidepressant effect, then other classes of antidepressant drug should have a similar effect. Confocal microscopic images of C6-2B cells treated with 10 µM fluoxetine for three days show a similar Gsµ staining pattern compared with desipramine-treated cells (FIG. 6A). The most striking similarity of desipramine and fluoxetine effects on $G_{s\alpha}$ localization is the loss of staining in the processes and process tips (compare FIGS. 6C and 6D, and FIG. 10A with FIGS. 6A and 6B). Approximately 100 cells were examined for qualitative differences as described above for FIG. 8. Of the fluoxetine-treated cells, 45% displayed intense staining in the process tips compared with the 64% of control and 32% of desipramine-treated cells mentioned previously.

Chlorpromazine

Figure 10B:
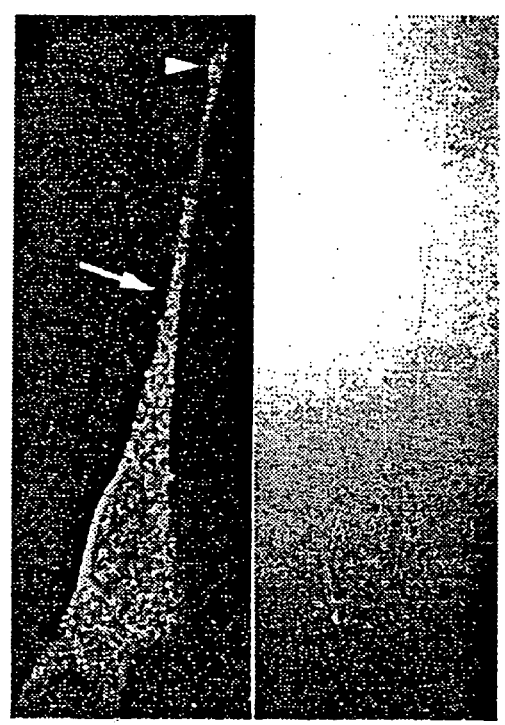

The antipsychotic drug chlorpromazine was used as a control for antidepressant effects. When cells were treated with 10 µM chlorpromazine for three days, $G_{s\alpha}$ staining was evident throughout the cell body (FIG. 10B): there is $G_{s\alpha}$ immunostaining throughout the cell body, cell process, and process tip. This pattern of $G_{s\alpha}$ distribution was similar to other control cells; 68% of approximately 100 cells demonstrated distinct staining in the cell processes and process tips.

Other Treatment Paradigms have a Similar Effect on $G_{s\alpha}$

A lower dosage and longer exposure time for desipramine treatment (3 µM for five day) was also tested. Control cells have intense staining at the process tips, whereas the desipramine treated cells do not. The main difference between the high-dose/three-day and the low-dose/five-day treatment regimens is the cell body localization of $G_{s\alpha}$. A majority of C6-2B cells treated with 10 µM desipramine display intense clustering of GsA in the perinuclear region whereas cells treated with 3 µM desipramine show a more even distribution between intense cell body staining and a more nondescript staining. One-day/10 µM desipramine treatment of C6-2B cells resulted in a $G_{s\alpha}$ distribution similar to cells treated with 3 µM for five days (data not shown). Under the acute treatment condition (one day, 10 µM) the number of cells lacking $G_{s\alpha}$ in the process tips was not significantly different from the control cell population seen in Table 4 and FIG. 8

EXAMPLE 13

Screening for Effectiveness of Antidepressant Therapy and Screening for Agents Having Antidepressant Activity In view of the foregoing results with respect to modifications noted in the association of $G_{s\alpha}$ with components of the plasma membrane or cytoskeleton from glioma cells, this example is directed to a method for detecting the effectiveness of antidepressant therapy as well methods for screening for agents having antidepressant activity.

An individual, diagnosed with major depression and receiving antidepressant therapy, may be assessed for the effectiveness of such therapy by the following method. Cells, for example, but not limited to blood cells [erythrocytes (red cells), leukocytes (white cells), platelets] and skin fibroblasts from peripheral tissues of the depressed individual are collected and a determination is made as to whether there has been a modification of the association of $G_{s\alpha}$ with components of the plasma membrane or cytoskeleton of cells from peripheral tissues of the depressed individual. Such modifications may include, but are not limited to enhanced coupling between $G_{s\alpha}$ and adenylyl cyclase, redistribution of $G_{s\alpha}$ from a strongly hydrophobic region of the plasma membrane to a less hydrophobic membrane domain, and/or redistribution of $G_{s\alpha}$ from cell processes and process tips to the cell body.

Antidepressent therapy often requires about one month to begin to achieve effectiveness. Often multiple drugs must be employed before a satisfactory combination is stumbled upon. Any difference in such modifications (as compared to a normal or control state), when noted in the early stages of antidepressant therapy and correlated with a subsequent decrease in the clinical depressive state would serve to quickly predict the success and/or failure of antidepressant therapy. More specifically, unlike psychological tests, if antidepressant therapy were to be effective, it is likely to increase such modifications in the association of $G_s\alpha$ with components of the plasma membrane or cytoskeleton within 3-5 days.

Further, the present invention is also useful for determining the effectiveness of a putative antidepressant agent or agents, in that such compounds may be rapidly screened using the methods described herein. Specifically, putative agents are introduced in a cell culture wherein the cells (for example, but not limited to Neuro2A cells (neuroblastoma), SKNSH cells (human blastoma) HEK293 cells (human embroynic kidney cells after transfection with Type VI adenylyl cyclase) express Type VI adenylyl cyclase and a determination is made as to whether there has been a modification (for example, but not limited to enhanced coupling between $G_{s\alpha}$ and adenylyl cyclase, redistribution of $G_{s\alpha}$ from a strongly hydrophobic region of the plasma membrane to a less hydrophobic membrane domain, and redistribution of $G_{s\alpha}$ from cell processes and process tips to the cell body of the association of $G_{s\alpha}$ with components of the plasma membrane or cytoskeleton of cells. Those agents that would be expected to have antidepressant activity would be those compounds that increase the modifications in the association of $G_{s\alpha}$ with components of the plasma membrane or cytoskeleton.

Further, the foregoing process lends itself to the use of fluorescence resonance energy transfer (FRET) techniques for use as a high throughput systems. We have recently developed a fluorescent analog of $G_{s\alpha}$ (a GPP fusion protein) for use in our experiments. Such an analog is used with a fluorescent adenylyl cyclase to determine the effects an antidepressant on the modification of interaction between Gsα and adenylyl cyclase. Specifically and in view of the foregoing examples and discussion, if the agent in question possessed antidepressant activity one would see an increase in FRET (an increased interaction between the fluorescent analog of $G_{s\alpha}$ and fluorescent adenylyl cyclase).

Although the present invention has been described in terms of preferred embodiments, it is intended that the present invention encompass-all modifications and variations that occur to those skilled in the art upon consideration of the disclosure herein, an in particular those embodiments that are within the broadest proper interpretation of the claims and their requirements.

All literature cited herein is incorporated by reference.

We claim:

1. A method for assaying for an agent or agents having an activity that modifies association of $G_{s\alpha}$ with components of the plasma membrane or cytoskeleton of cells comprising the step of:
    (a) contacting said agent or agents with cultured cells;
    (b) determining whether there has been a modification of association of $G_{s\alpha}$ with components of the plasma membrane or cytoskeleton of the cells in step (a) via comparison to a control cell culture lacking said agent or agents;
    (c) identifying agents that modify the association of $G_{s\alpha}$ with components of the plasma membrane or cytoskeleton of cells from a difference in the modification of the association of $G_{s\alpha}$ with components of the plasma membrane or cytoskeleton of the cells in step (a).

2. A method for assaying for an agent or agents having antidepressant activity comprising the step of:
    (a) contacting said agent or agents with cultured cells;
    (b) determining whether there has been a modification of association of a fluorescent $G_{s\alpha}$ analog with components of the plasma membrane or cytoskeleton of the cells in step (a) via comparison to a control cell culture lacking said agent or agents;
    (c) identifying agents having antidepressant activity from a difference in the modification of the association of the fluorescent $G_{s\alpha}$ analog with components of the plasma membrane or cytoskeleton of the cells in step (a), wherein an agent or agents having antidepressant activity increases the modification of the association of fluorescent $G_{s\alpha}$ analog with components of the plasma membrane or cytoskeleton of the cells in step (a).

3. The method of claim 2 wherein the modification is enhanced coupling between the fluorescent $G_{s\alpha}$ analog and adenylyl cyclase.

4. The method of claim 3 wherein the adenylyl cyclase is fluorescently labeled.

5. The method of claim 4, wherein the interaction between the fluorescent $G_{s\alpha}$ analog and the fluorescently labeled adenylyl cyclase is monitored using fluorescence resonance energy transfer (FRET) wherein an increase in FRET is observed when said agent or agents possess antidepressant activity.

* * * * *

UNITED STATES PATENT AND TRADEMARK OFFICE
CERTIFICATE OF CORRECTION

PATENT NO. : 7,445,888 B2  Page 1 of 1
APPLICATION NO. : 11/529944
DATED : November 4, 2008
INVENTOR(S) : Mark M. Rasenick et al.

It is certified that error appears in the above-identified patent and that said Letters Patent is hereby corrected as shown below:

On the Cover Page:

Item (*), add -- This patent is subject to a terminal disclaimer --.

Signed and Sealed this

Twenty-fourth Day of March, 2009

JOHN DOLL
*Acting Director of the United States Patent and Trademark Office*